United States Patent
Mohl et al.

(10) Patent No.: US 11,672,660 B2
(45) Date of Patent: Jun. 13, 2023

(54) ANNULOPLASTY DEVICE

(71) Applicant: AVVIE GMBH, Vienna (AT)

(72) Inventors: Werner Mohl, Altenmarkt-Thennenberg (AT); Ashly Shaji, Vienna (AT)

(73) Assignee: AVVIE GMBH, Vienna (AT)

( * ) Notice: Subject to any disclaimer, the term of this patent is extended or adjusted under 35 U.S.C. 154(b) by 0 days.

(21) Appl. No.: 17/909,668

(22) PCT Filed: Mar. 2, 2021

(86) PCT No.: PCT/IB2021/051721
§ 371 (c)(1),
(2) Date: Sep. 6, 2022

(87) PCT Pub. No.: WO2021/176344
PCT Pub. Date: Sep. 10, 2021

(65) Prior Publication Data
US 2023/0120494 A1    Apr. 20, 2023

(30) Foreign Application Priority Data

Mar. 3, 2020   (EP) ..................................... 20020094

(51) Int. Cl.
*A61F 2/24*        (2006.01)

(52) U.S. Cl.
CPC .......... *A61F 2/2445* (2013.01); *A61F 2/2442* (2013.01); *A61F 2/2448* (2013.01);
(Continued)

(58) Field of Classification Search
CPC .... A61F 2/2442; A61F 2/2445; A61F 2/2448; A61F 2/2466
See application file for complete search history.

(56) References Cited

U.S. PATENT DOCUMENTS

| | | | |
|---|---|---|---|
| 7,507,252 B2 * | 3/2009 | Lashinski | A61F 2/2466 623/2.37 |
| 2013/0226290 A1 * | 8/2013 | Yellin | A61F 2/2448 623/2.11 |

(Continued)

OTHER PUBLICATIONS

International Search Report and Written Opinion received in PCT/IB2021/051721 dated May 18, 2021, pp. 15.

(Continued)

*Primary Examiner* — William H Matthews
(74) *Attorney, Agent, or Firm* — Liang & Hennessey LLP; Brian Hennessey

(57) ABSTRACT

Annuloplasty device for use on a posterior annulus of a mitral valve, which is deployable to the mitral valve by means of a vascular delivery device, such as a catheter, and positionable along the curvature of the annulus, including at least a first and a second branch, each configured to extend along at least a section of the annulus, with a first end and a second end, at least one guiding means for guiding the first and the second branches relative to one another, at least one fixing means for fixing the device to the annulus, and at least one anchor means arranged on each of the first and second branches, whereby the first and the second branches are movable relatively to one another, so that the anchor means engage with the annulus thereby pulling the annulus together when the first and second branches are moved in opposite directions.

12 Claims, 10 Drawing Sheets

(52) U.S. Cl.
CPC .... *A61F 2/2466* (2013.01); *A61F 2220/0016* (2013.01); *A61F 2250/0008* (2013.01)

(56) References Cited

U.S. PATENT DOCUMENTS

2019/0125325 A1     5/2019   Sheps et al.
2019/0336288 A1*   11/2019   Gross .................... A61F 2/2445
2020/0015970 A1     1/2020   Solem et al.

OTHER PUBLICATIONS

International Preliminary Report received in PCT/IB2021/051721 dated Jan. 28, 2022, pp. 1-7.

* cited by examiner

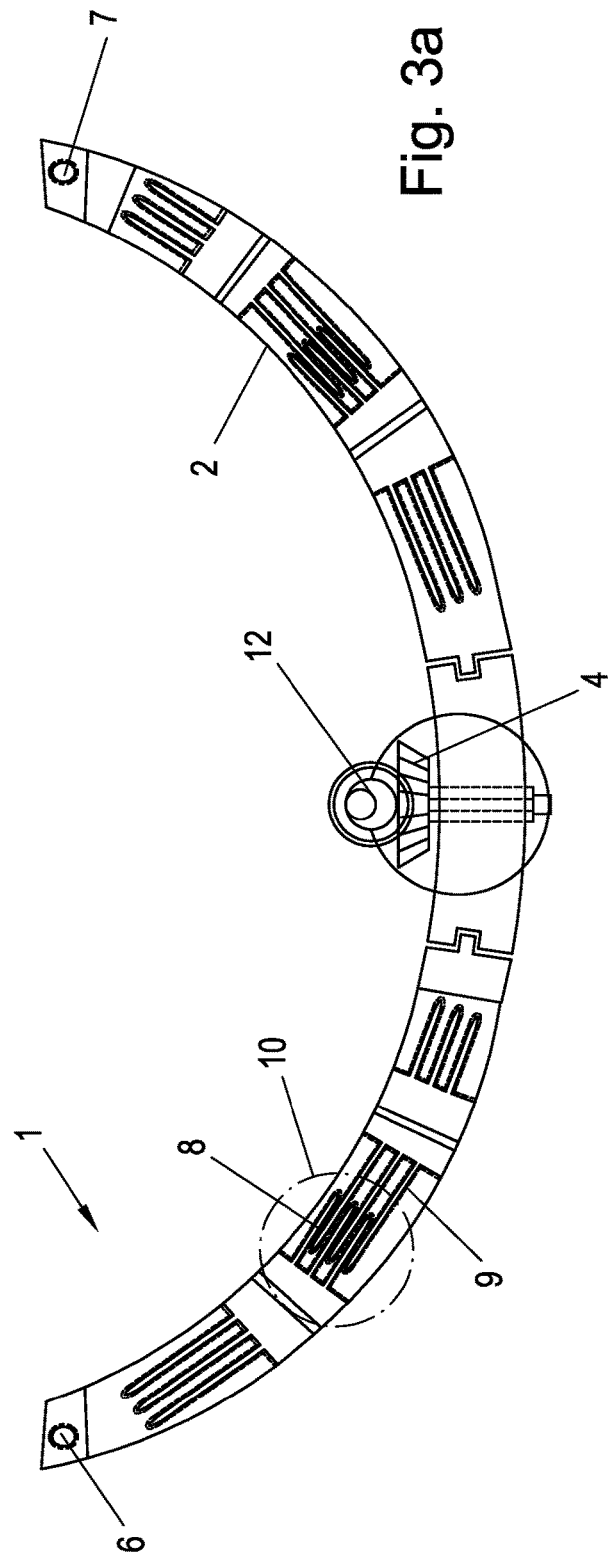
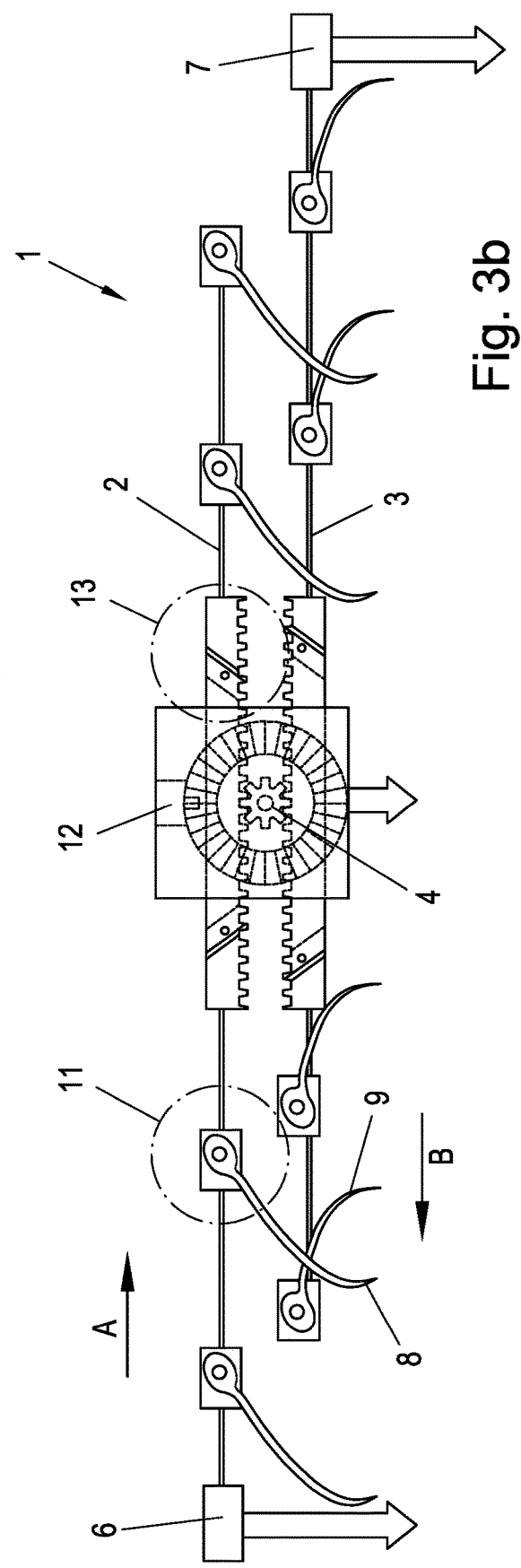

ANNULOPLASTY DEVICE

CROSS-REFERENCE TO RELATED APPLICATIONS

The present application is a national phase application of PCT Application No. PCT/IB2021/051721, filed Mar. 2, 2021, entitled "ANNULOPLASTY DEVICE", which claims the benefit of European Patent Application No. 20020094.7, filed Mar. 3, 2020, each of which is incorporated by reference in its entirety.

BACKGROUND OF THE INVENTION

1. Field of the Invention

The invention refers to an annuloplasty device for use on a posterior annulus of a mitral valve, which is deployable to the mitral valve by means of a vascular delivery device, such as a catheter, and positionable along the curvature of the annulus.

2. Description of the Related Art

The mitral valve is situated in the left heart between the left atrium and the left ventricle. It comprises two leaflets, namely an anterior and a posterior leaftlet, which are divided by two commissures, namely an anterolateral commissure (AC) and a posteromedial commissure (PC). The anterior leaflet is divided in 3 areas, namely A1, A2 and A3 and the posterior leaflet is divided in three areas, namely P1, P2 and P3. The opening of the mitral valve is surrounded by the mitral annulus, which is a fibrous ring that is attached to the mitral valve leaflets. The mitral annulus is saddle shaped and contracts and reduces its surface area during systole in order to aid complete closure of the leaflets. Pathological expansion of the annulus, such as gaps between P1 and P2 or P2 and P3, which are caused by dilation/stretching of the annulus, can result in malcoaptation of the anterior and posterior leaflets, i.e. in leaflets that do not close properly, which causes mitral insufficiency.

Under normal conditions, blood flows through an open mitral valve during diastole with contraction of the left atrium, and the mitral valve closes during systole with contraction of the left ventricle. The valve opens and closes because of the pressure differences prevailing in the heart, i.e. the mitral valve opens when there is greater pressure in the left atrium than in the ventricle, and closes when there is greater pressure in the ventricle than in the atrium.

The mitral annulus changes in shape and size during the cardiac cycle. Due to the contraction of the left atrium the mitral annulus is smaller at the end of atrial systole, like a sphincter, which is important for proper coaptation of the leaflets of the mitral valve when the left ventricle contracts and pumps the blood.

There are several causes of mitral insufficiency including changes in leaflet structure, annulus dilatation or dilation of the subvalvular apparatus.

Annulus dilatation may be due to pressure and volume overload in the ventricle, which may be caused by mitral insufficiency and heart failure, contraction abnormalities and myocardial scarring after myocardial infarction.

A constant volume overload in the ventricle may lead to an increase in the ventricle size. The increased ventricle causes a dilated subvalvular apparatus (chordae tendinae and papillary muscles), whereby the dilated subvalvular apparatus especially pulls the posterior leaflet towards the ventricle. The anterior leaflet may also be pulled towards the ventricle. Thereby a coaptation gap between the anterior and posterior leaflet as well as between the cusps P1 and P2 and between P2 and P3 as well as near the commissures occurs, which results in severe mitral insufficiency.

Dilatation of the posterior annulus hence results in leaking valves that can be corrected by mitral valve annuloplasty, which aims at restoring proper leaflet adjustment. Annuloplasty devices are fixed to the annulus, preferably the posterior annulus, of the mitral valve and are normally used to reduce the circumferential length of the pathologically stretched annulus of the mitral valve by 20-30%, which then allows for correct coaptation of the mitral valve.

State of the art annuloplasty devices, such as e.g. annuloplasty rings and bands, require utmost surgical skills of the surgeon, since the band is to be sutured in such a way to the dilated annulus that its shape is reconstructed from a circular diseased shape to an ellipsoid shape mimicking the geometry of a normal competent valve and heart valve functionality is effectively restored. Although many rings and bands are available according to the disease status and surgical experience, annuloplasty rings and bands have standardized dimensions, which limit the scope of action of the surgeon. Hence, the possibility of taking individual needs of a patient, which may be caused by variations in the anatomical structure of the annulus or variations in the pathological expansion pattern of the annulus, cannot be taken into account properly. The implantation of state of the art annuloplasty bands might hence result in a degree of contraction which is too high in one area of the annulus, and a degree of contraction which is too little in another area. After implantation of state of the art annuloplasty bands, proper heart valve functionality can therefore not be guaranteed.

SUMMARY OF THE INVENTION

Hence, it is an object of the instant invention to provide an improved annuloplasty device, which takes into account the individual needs of the patient and provides for a reliable reconstruction of the dilated annulus by taking into account the variations in the anatomical shape or variations in the pathological changed shape of the annulus, respectively.

In order to achieve said objects, the annuloplasty device according to the invention comprises at least a first and a second branch, each configured to extend along at least a section of the annulus, with a first end and a second end, at least one guiding means for guiding the first and the second branches relative to one another, at least one fixing means for fixing the device to the annulus, and at least one anchor means arranged on each of the first and second branches, whereby the first and the second branches are arranged to be movable relatively to one another, so that the anchor means engage with the annulus thereby pulling the annulus together when the first and second branches are moved in opposite directions. Said movement allows the change of the distorted, circular shaped annulus into the anatomically correct ellipsoid form facilitating sufficient coaptation and therefore valve competency.

The annuloplasty device according to the invention can alternatively be used on a tricuspid valve, preferably on a mural leaflet of a tricuspid valve.

The invention provides an improved annuloplasty device that reduces annulus dimensions and increases the leaflet coaptation. In particular, the annuloplasty device of the invention reduces the septal-lateral mitral annular diameter by cinching along the perimeter of the annulus. Cinching is achieved by the first and a second branches that each carry at least one anchor means that interacts with the annulus. Upon a relative movement of the first and second branches, the anchor means pull the tissue of the annulus in opposite directions so that cinching occurs. Since the relative movement of the two branches defines to what degree the annulus is cinched, human annuli, which show different stretching degrees and/or different pathoanatomical shapes, can be effectively treated. For example, in the case of heavily dilated or asymmetric annuli a larger movement of the two branches relatively to one another provides for a higher degree of cinching than in the case of less dilated annuli. Hence, the annuloplasty device according to the invention provides for individual reduction properties according to the individual patient's needs.

For example, the annuloplasty device according to the invention provides for a reduction of the circumference of the annulus by 20-30%.

The at least one fixing means provides for an initial connection of the device to the annulus. Preferably, said fixing means is arranged in the middle of the device and may preferably be connected to the center of the P2 region of the posterior leaflet of the mitral valve.

Due to the relative movement of the branches the anchor means move along the curvature of the annulus thereby engaging with the tissue.

Preferably, at least one, more preferably all, of the individual components of the device may be made of a shape-memory alloy, preferably Nitinol.

Preferably, the first and the second branches are movably guided in the guiding means, and the device further comprises a first pulling means arranged on the first end of the first branch and a second pulling means arranged on the first end of the second branch, whereby the first ends of the two branches are arranged opposite to one another, and the relative movement of the branches is achieved by pulling the pulling means in opposite directions.

The pulling means preferably comprise electro magnets and/or electro-active polymers and/or a pneumatic means and/or a vacuum chamber and/or wires.

The pulling means may be connected to a mechanical or electric command line that extends through the delivery device, such as a catheter, to an extracorporeal control device that allows the surgeon to initiate and control the pulling action exerted by the pulling means.

Alternatively, a gear is provided for driving the first and the second branches to move relative to each other. Preferably, the gear is configured as a toothed gear comprising a drive pinion that engages with a toothed rack on each of the first and second branches. Preferably, a gear translates a rotational movement into a longitudinal movement.

In order to optimally arrange the device and to provide an even more reliable connection to the annulus, a second and a third fixing means are preferably provided, whereby the center of the device carries the first fixing means, the first end of the first branch carries the second fixing means, and the first end of the second branch carries the third fixing means, whereby the first ends of the two branches are arranged opposite to one another. With said preferred configuration the first fixing means may be fixed to the P2 region of the posterior leaflet of the mitral valve and the second and the third fixing means may effectively bind to the AC and PC region of the valve. Thereby the device may be arranged and fixed in the perfect position for the subsequent reshaping of the annulus.

Preferably, only a first and a second fixing means is provided, whereby the fixing means either engage with P2 and AC or P2 and PC and the regions lying between P2 and AC or P2 and PC, respectively, are effectively cinched. Said embodiment may be used when the annulus does not show an overall dilation, but only dilations in some of its regions.

Preferably, the fixing means are formed by clamps and/or pliers and/or needles and/or hooks and/or pins. Clamps and pliers both serve for grabbing the annulus. In the case of pliers the tissue may be penetrated, whereby an even stronger fixation of the device to the annulus is realized. In the case of needles, hooks or pins the tissue is also penetrated. To mimic the natural shape of the annulus, the at least one first and second branches are preferably half-ring shaped.

The branches may be built as half-ring shaped rails or, alternatively may be built as strings, whereby the anchor means are arranged on the strings and the strings are connected to the guiding means.

Preferably, the strings are built by shape retaining metal wires. Alternatively, the at least one first and second branches may preferably be formed as memory shaped half-ring rails. The memory shape material provides for the possibility that the half-ring shape of the branches is not deployed until the release of the branches from the deployment instrument.

Preferably, the two branches comprise interacting guiding profiles for guiding the first branch relative to the second branch.

The anchor means may preferably be anything capable of properly securing the device to the heart tissue, such as needles and/or hooks and/or clips and/or staples and/or rivets. Preferably, the anchor means are barbed to strengthen the attachment to the tissue.

To effectively prevent the tissue from tearing and to prevent the anchor means from detaching from the tissue, the anchor means may preferably have a trident shape, which enables secure attachment of the anchor means to the valve tissue.

To provide for effective cinching of the annulus, the at least one anchor means of the first branch is preferably oriented in a direction opposite to a direction of the at least one anchor means of the second branch. When the two branches are moved relatively to one another after the fixing of the device to the tissue, the tissue between the oppositely oriented anchor means is effectively cinched.

Preferably, the anchor means are arranged such that they crisscross without obstructing each other's movement.

To enhance the attachment and the cinching properties of the device, a plurality of anchor means is preferably arranged on each of the first and the second branches. The more anchor means are fixed to each of the branches the more attachment points between the device and the valve tissue are established, which results in a more reliable connection of the device to the tissue. Additionally, more individual cinching areas between the individual anchor means are established, thereby better attending to individual patients needs and achieving a higher degree of diameter reduction of the annulus. The plurality of anchor means may penetrate in different locations along the fibrous skeleton of the annulus and the atrium to prevent tearing of the tissue. Pulling together of functionally conjoined identical anchor means on both branches allows an even distribution of forces similar to a surgical repair. Contrary to state of the art transcatheter cinching devices, with which the pulling in one direction only provides for a circular cinching of the annulus, said preferred embodiment favors an ellipsoid shape displacing the posterior aspect of the annulus towards the coaptation zone.

The anchor means are preferably deployable from a first position, in which the anchor means are retracted for being arranged within a delivery device, into a second position, in which the anchor means are deployed. Since the device is implanted in the heart by the aid of e.g. a catheter, the retracted position of the anchor means helps to realize a space-saving embodiment of the device, which easily fits into a catheter. When being pushed out of the delivery device, the anchor means deploy and subsequently attach to the tissue when the branches are moved relatively to one another.

The annuloplasty device according to the invention may be deployed with the aid of a delivery device.

To avoid damaging of the delivering device during delivery of the device to the heart and to avoid attachment of the device to other tissues than the annulus, the device preferably comprises covering means. The covering means are fixed to one of the first or second branches and enclose the anchor means, when being in the first, retracted position. When the first branch, which carries the covering means, is moved relative to the second branch, the anchor means are uncovered and thereby deploy, which results in that the anchor means engage with the tissue during the movement of the branches.

Preferably, the covering means are ring-shaped.

In a separate aspect of the present invention, a delivery device for delivering and deploying the annuloplasty device to the annulus of the mitral valve is provided, comprising at least one flexible tube, in which the annuloplasty device is housed prior to being delivered, a guiding wire for guiding the flexible tube to the annulus and retracting means for retracting the flexible tube relative to the at least first and second branches of the annuloplasty device so as to release the branches from the flexible tube.

The implantation of the annuloplasty device may be realized via e.g. transcatheteral delivery, whereby the flexible tube, which houses the annuloplasty device, is delivered to the implantation site in the human heart. Correct delivery of the flexible tube to the annulus is guided with the aid of a guiding wire, which is connected to the delivery device and/or the annuloplasty device and which is steerable by the means of the catheter. When the implantation site is reached, the flexible tube has to be retracted, whereby the retraction is realized by retracting means, which are also steerable by the means of the catheter.

Preferably, the delivery device comprises a pusher, which may be pressed onto the fixed annuloplasty device, thereby preventing it from being detached from the annulus during the cinching process.

Further, the annuloplasty device may preferably be connected to another device for mitral valve repair, such as an artificial leaflet. The other device is preferably to be fixed in the region of the P2 segment of the mitral valve, i.e. connected to the center of the annuloplasty device, which carries the first fixing means. The connection between the two devices is preferably achieved by the use of a connector. The connector may be fixed to the annuloplasty device and has a free end, preferably a free end built as a slit. Said free end may interact with a free end of a connecting needle, preferably a free end built as a pin, which is fixed to the artificial leaflet and may be introduced into the slit of the connector of the annuloplasty device. Thereby a reliable connection of the two devices may be achieved.

Alternatively, the slit may be arranged on the artificial leaflet and the pin may be arranged at the annuloplasty device.

Fixing of the individual devices to the damaged heart tissue may be done as follows.

In a first step the annuloplasty device and the artificial leaflet are delivered to the annulus with the aid of e.g. a catheter.

In a second step the annuloplasty device is fixed onto the annulus and deployed and moved to fulfill its function of shortening the annulus.

In a third step the artificial leaflet is deployed and its connecting needle is introduced in the slit of the connector of the annuloplasty device and locked.

Then the catheter is withdrawn from the heart.

To be able to take individual patients needs into account and to treat different stages of annuli dilation, a planning algorithm is preferably provided. The algorithm serves to convert echo data from an echocardiography into measurements for constructing individual annuloplasty devices, which exactly fit to the patients needs.

The algorithm preferably comprises the following steps:

Echo data is retrieved.

The distance between the individual regions of the annulus (AC, P1, P2, P3, PC) is determined from evaluating the echo data.

The posterior leaflet circumference is determined.

The gap in coaptation is determined.

The binding of the center of the device to the posterior leaflet is simulated.

The binding of the device to the AC and PC region of the valve is simulated.

The closing of the gap is simulated by the movement of the posterior leaflet towards the anterior leaflet, whereby the movement is performed until the anterior leaflet is reached and the gap in coaptation is closed, thereby simulating the shortage of the circumference of the annulus.

The annuloplasty device is constructed for compensating the gap.

With said algorithm the distance between the anchor means of the device may be exactly determined and a device, which exactly fits to individual patient needs, may be constructed. Hence, with the aid of said algorithm an indication to which extent the annulus has to be cinched is established, which simplifies the surgical intervention already beforehand.

BRIEF DESCRIPTION OF THE DRAWINGS

In the following the present invention will be described by some exemplary embodiments.

FIG. 3b is a front view of the embodiment as depicted in FIG. 3a, FIG. 4a is a top view of the second exemplary embodiment of the annuloplasty device according to the invention as depicted in FIG. 3a after cinching of the annulus was performed.

DETAILED DESCRIPTION

Figure 1B:
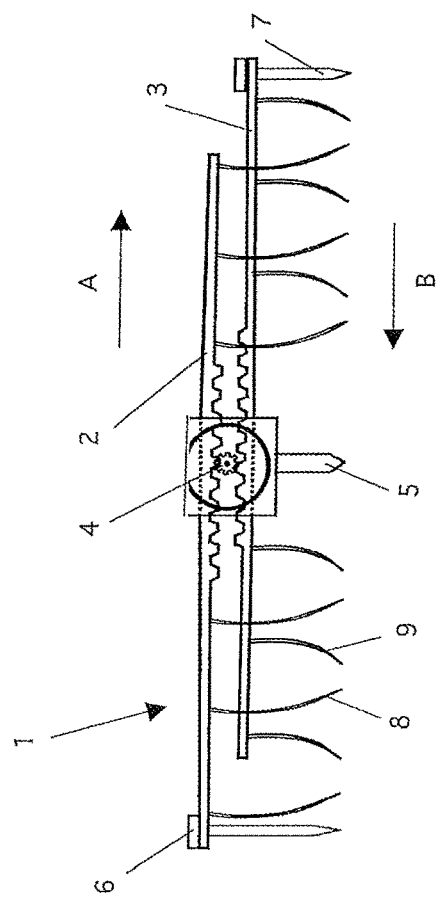
FIG. 1b is a front view of the embodiment as depicted in FIG. 1a, FIG. 2a is a top view of the first exemplary embodiment of the annuloplasty device according to the invention as depicted in FIG. 1a after cinching of the annulus was performed.
Figure 1A:
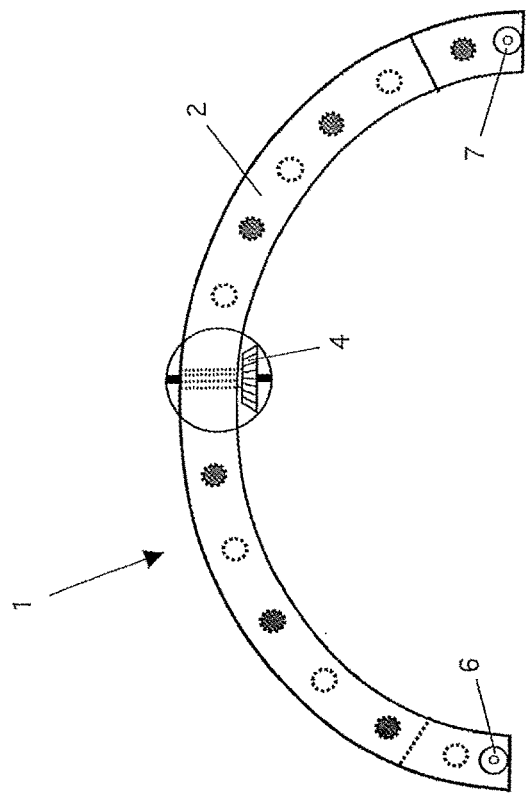
FIG. 1a is a top view of a first exemplary embodiment of the annuloplasty device according to the invention before cinching of the annulus is performed.

In FIGS. 1a and 1b the first exemplary embodiment of the annuloplasty device according to the invention is marked with reference numeral 1. The annuloplasty device 1 comprises a first branch 2 and a second branch 3, which are built as substantially half-ring shaped rails. Further, the device 1 comprises a guiding means 4 comprising a gear for guiding and driving the first branch 2 and the second branch 3 relative to one another according to arrows A and B. The annuloplasty device 1 comprises three fixing means 5, 6 and 7 for fixing the device to the annulus, whereby the center of the device 1 carries the first fixing means 5, a first end of the first branch 2 carries the second fixing means 6, and a first end of the second branch 3 carries the third fixing means 7.

On the first branch 2 a plurality of anchor means 8 is arranged and on the second branch 3 a plurality of anchor means 9 is arranged, whereby the anchor means 8 of the first branch 2 are oriented in a direction opposite to the anchor means 9 of the second branch 3.

Figure 2B:
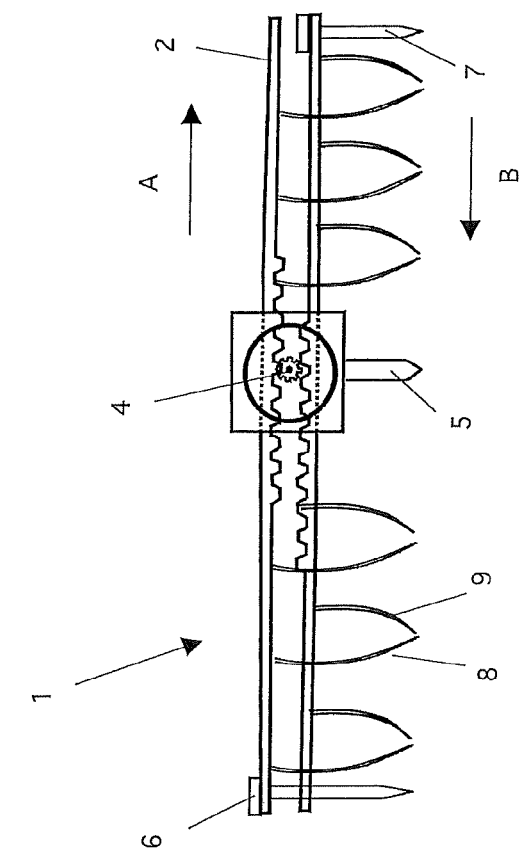
FIG. 2b is a front view of the embodiment as depicted in FIG. 2a, FIG. 3a is a top view of a second exemplary embodiment of the annuloplasty device according to the invention before cinching of the annulus is performed.
Figure 2A:
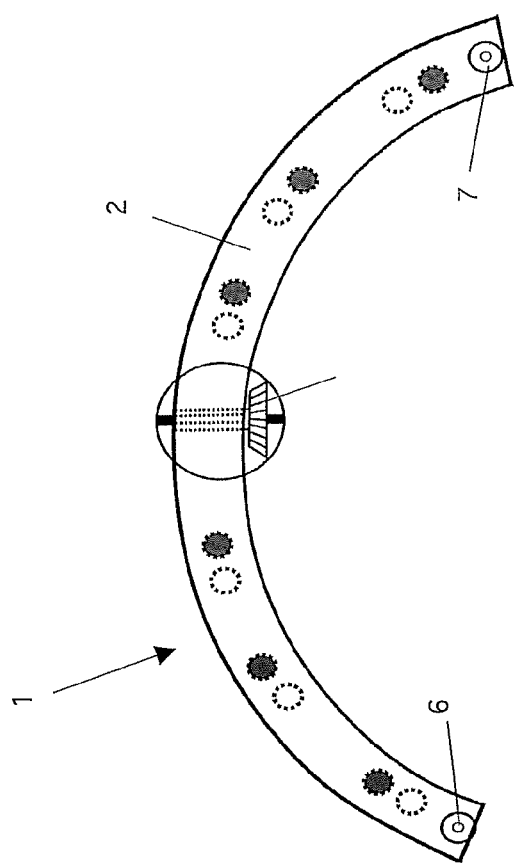

FIGS. 2a and b show the first exemplary embodiment of the annuloplasty device according to FIGS. 1a and b after cinching of the annulus was performed, i.e. after the first branch 2 was moved according to arrow A and the second branch 3 was moved according to arrow B. By said relative movement the anchor means 8,9 engage with the annulus and move towards each other, thereby cinching the tissue between the anchor means, which results in reduction of the circumference of the annulus.

Figure 4A:
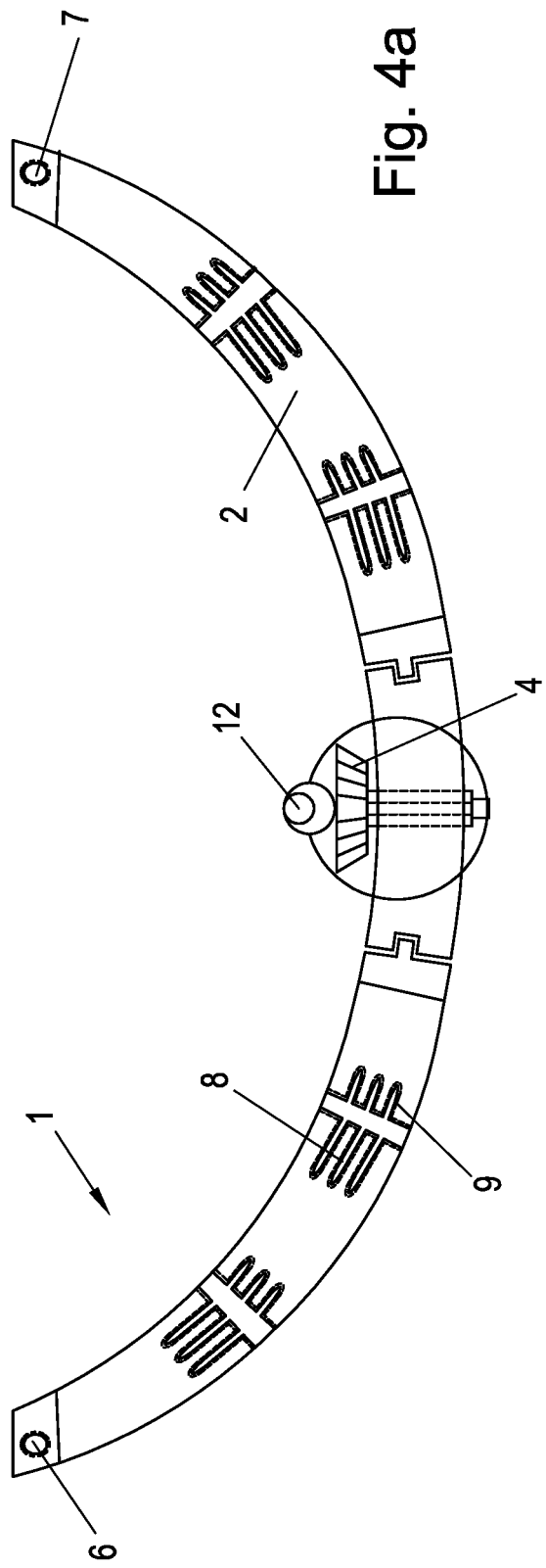
FIG. 4b is a front view of the embodiment as depicted in FIG. 3a, FIG. 5 is a front view of the second embodiment of the present invention as depicted in FIG. 3 and FIG. 4 in its folded state.
Figure 4B:
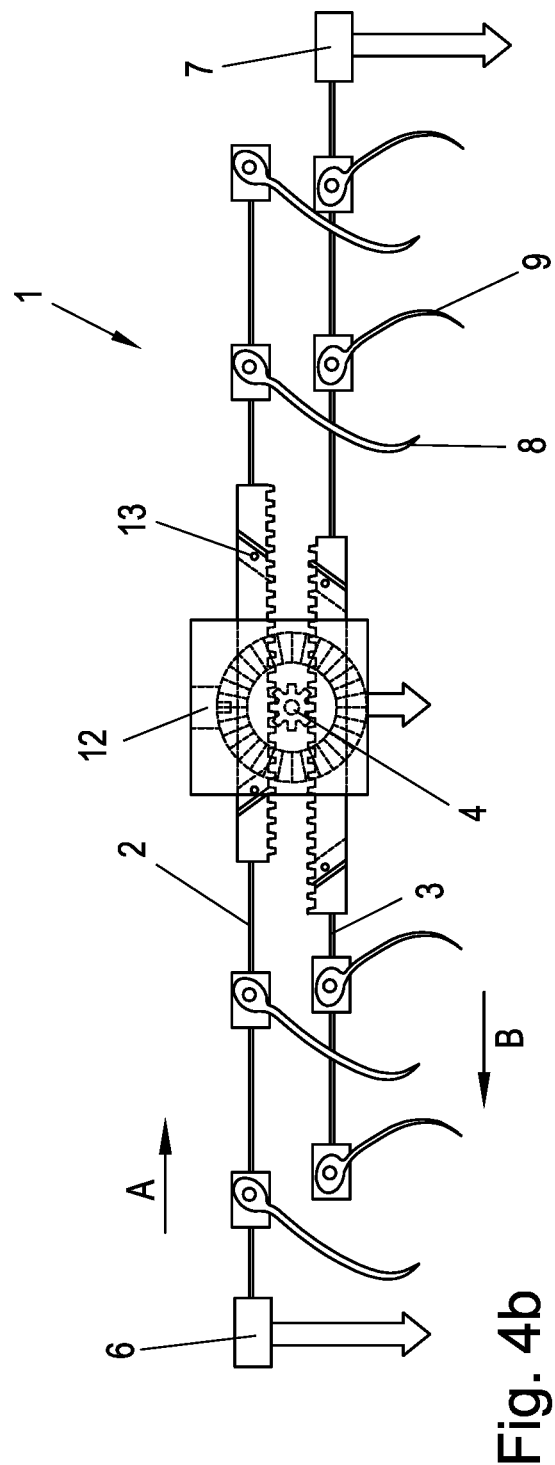

In FIG. 3 and FIG. 4 the same reference numerals are kept for same parts of the device as used in FIG. 1 and FIG. 2.

FIG. 3 shows a second exemplary embodiment of the annuloplasty device according to the invention before cinching of the annulus is performed.

The branches 2 and 3 are built as strings, whereby the anchor means 8 and 9 are arranged on the strings (as highlighted by circle 11). The strings 2 and 3 are connected to the gear 4 and preferably built by shape retaining metal wires. The device 1 is fixed to the heart tissue by fixing means 6 and 7.

As marked with circle 10, the anchor means 8 and 9 are arranged such that they crisscross without obstructing each other's movement. The anchor means are positioned in such a way (oblique from a first position and to both branches), that they may optimally ingress the fibrous skeleton and the atrial myocardium to avoid perforation or rupture of the tissue.

Further, FIG. 3 shows a connector 12, which provides a free end for introducing e.g. a connecting needle of a second device (not shown), which is to be connected to the annuloplasty device.

Circle 13 marks a hinge mechanism, which serves to fold branches 2 and 3 when being delivered to the heart (cf. FIG. 5) and to unfold the branches when the device is deployed. FIG. 3 shows the device in its unfolded, deployed position, i.e. when exiting the deployment catheter.

FIG. 4a shows the second exemplary embodiment of the annuloplasty device according to the invention as depicted in FIG. 3 after cinching of the annulus was performed, i.e. after the first branch 2 was moved according to arrow A and the second branch 3 was moved according to arrow B. Said movement is performed after the fixation of the device 1 with fixing means 6 and 7 as described above with regard to FIG. 3 took place. Due to their connection to the branches 2 and 3 the anchor means 8,9 automatically unfold during the movement of the branches, since their unfolding mechanism is also driven by the gear 4 which drives the movement of the branches.

Figure 5:
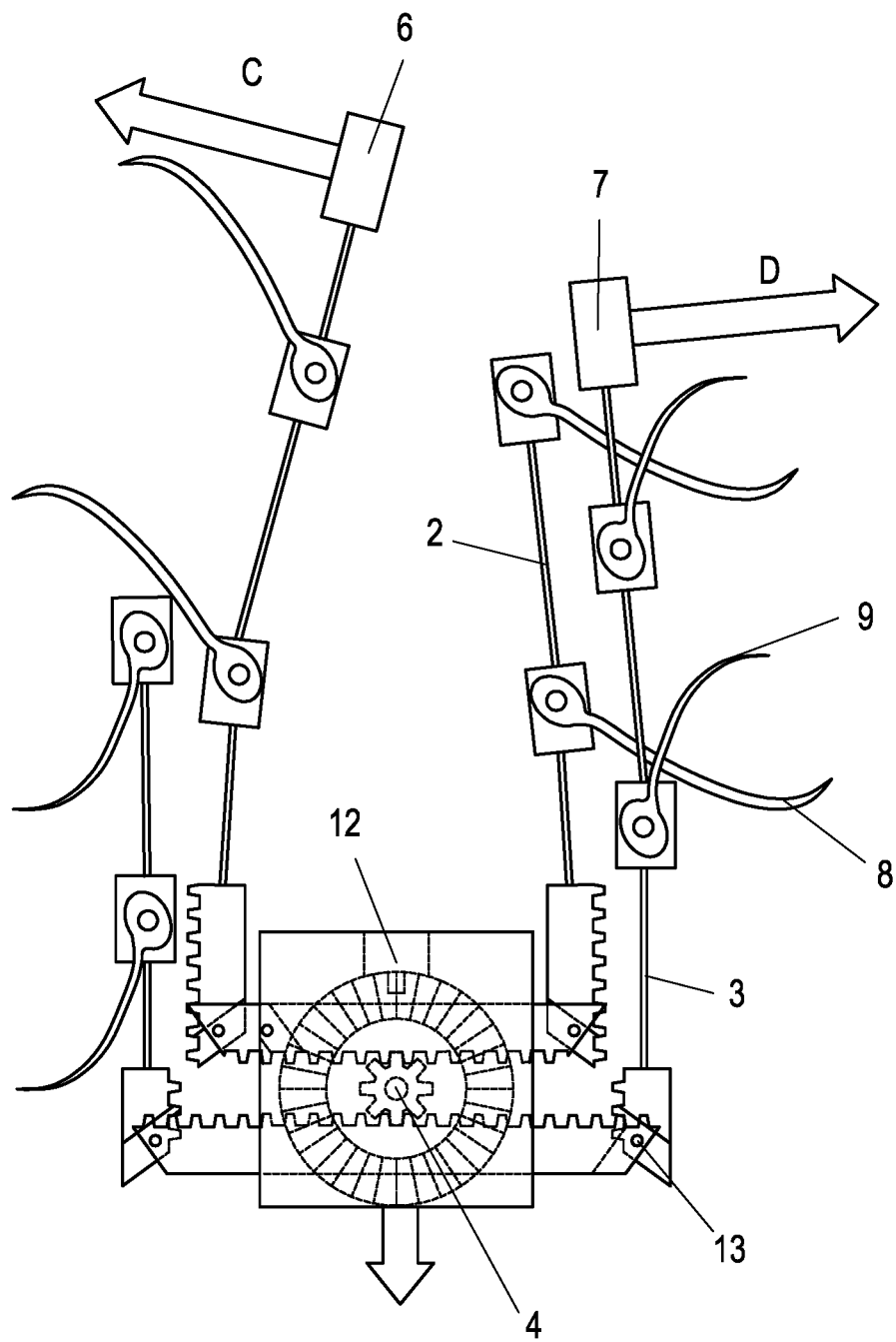

FIG. 5 is a front view of the second embodiment of the present invention as depicted in FIGS. 3 and 4 in its folded state. The hinge mechanism 13 is shown in its folded position, which serves to fold branches 2 and 3 so that the device is reduced in its dimensions for being placed in a catheter sleeve.

After being delivered to the heart, unfolding of the branches 2 and 3 is achieved by pulling the branches according to arrows C and D.

FIG. 6a shows an isometric view of a third embodiment of the invention before cinching of the annulus is performed. The annuloplasty device 1 again comprises a first branch 2 and a second branch 3 which are substantially half-ring shaped and slidably guided in a guiding means 4. Contrary to the first and the second embodiment, the two branches comprise interacting guiding profiles 14 and 15 for guiding the first branch 2 relative to the second branch 3 in direction of arrows A and B.

FIG. 6b shows the third embodiment as depicted in FIG. 6a fixed to the curvature of a dilated annulus, i.e. before cinching is performed. The gap in coaptation between the anterior leaflet 16 and P1, P2 and P3 of the posterior leaflet 17 of the mitral valve is marked with reference number 18.

Figure 7:
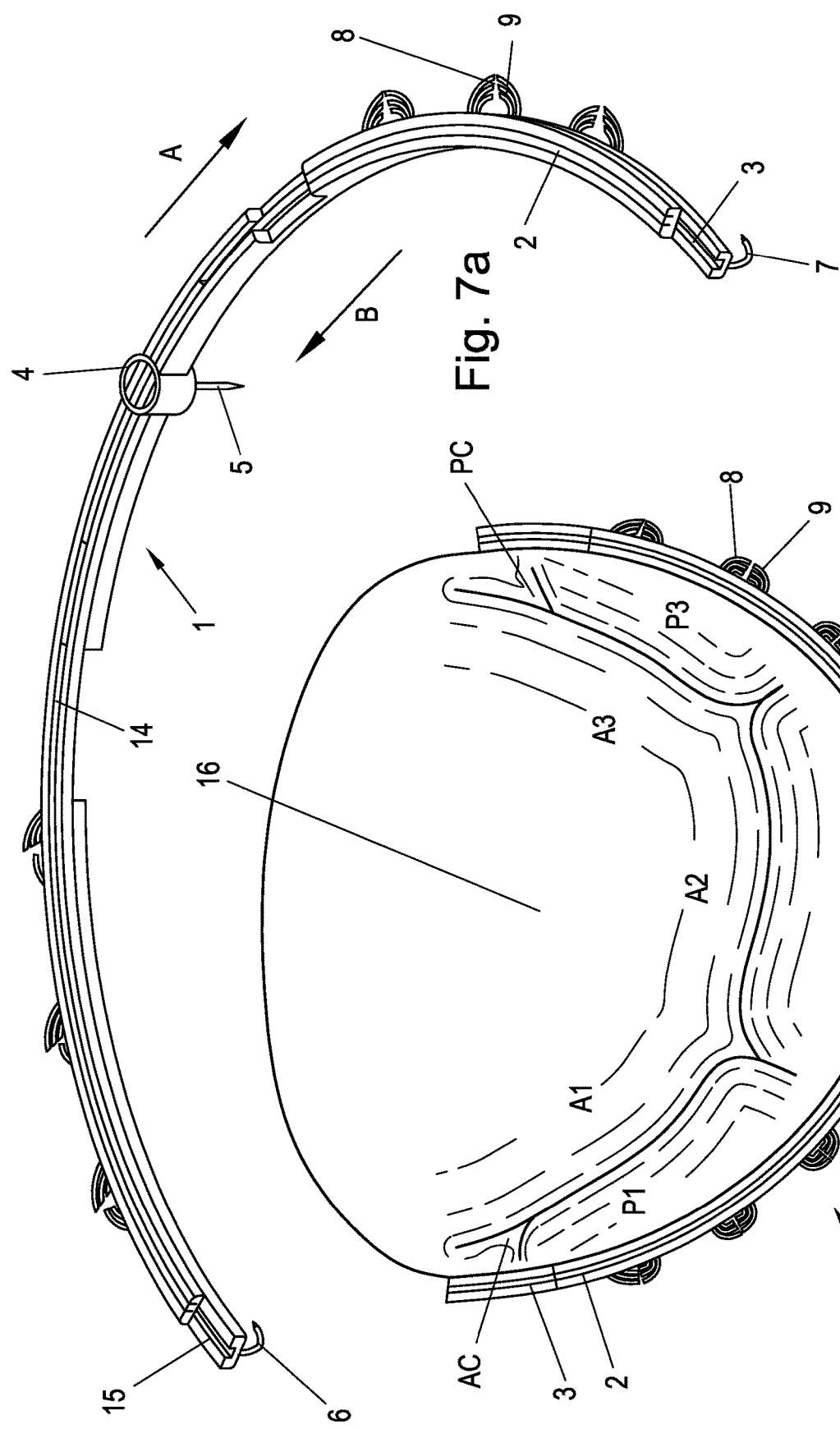
FIG. 7a shows an isometric view of the third exemplary embodiment of the invention after cinching was performed.
FIG. 7b shows the third embodiment as depicted in FIG. 7a fixed to a shortened annulus.

FIG. 7a shows an isometric view of the third embodiment of the invention after the cinching of the annulus was performed, i.e. after the branches were moved according to arrows A and B.

Figure 6:
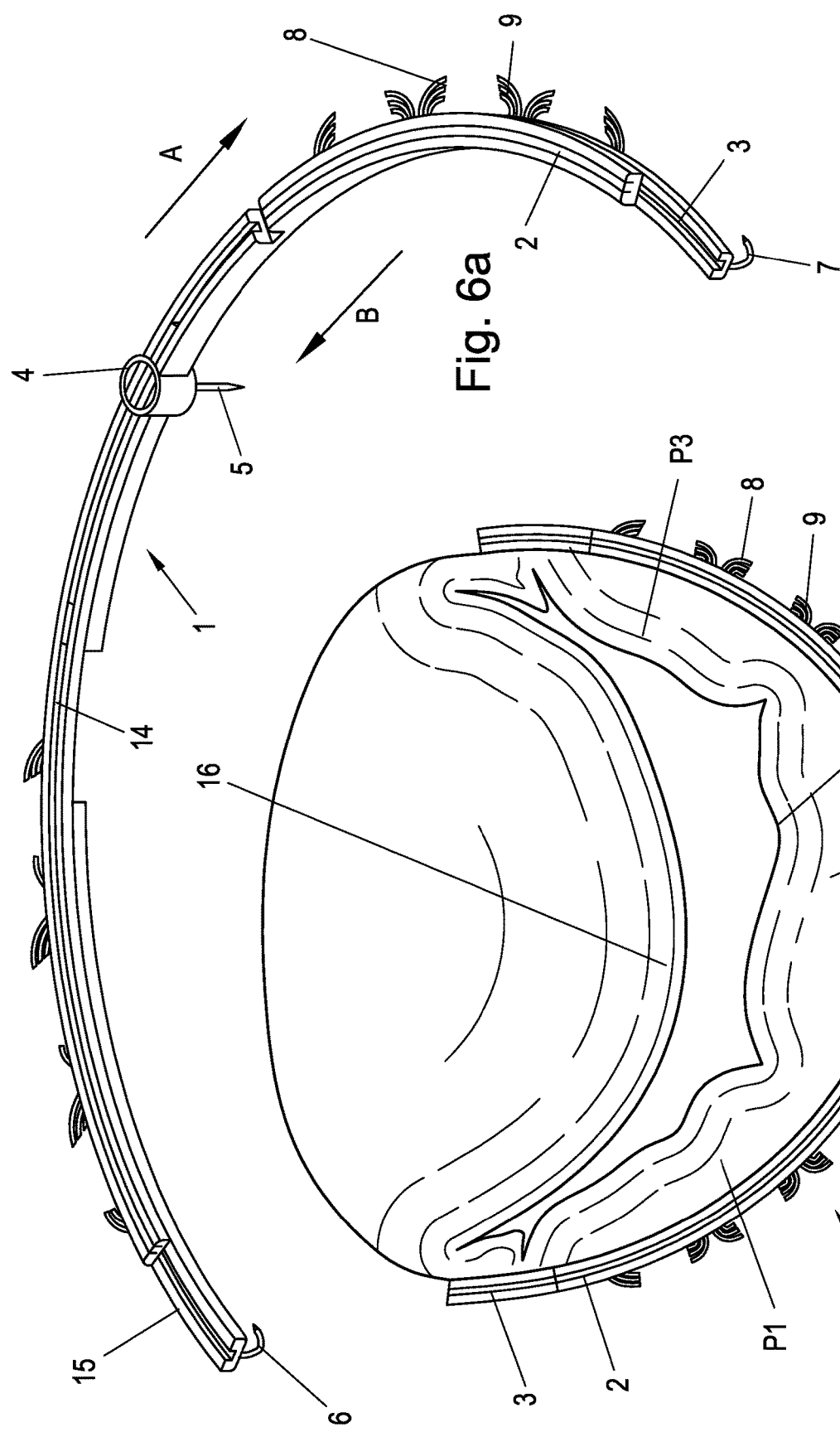
FIG. 6a shows an isometric view of a third exemplary embodiment of the invention before cinching is performed.
FIG. 6b shows the third embodiment as depicted in FIG. 6a fixed to a dilated annulus.

FIG. 7b shows the third embodiment as depicted in FIG. 7a with shortened segments P1, P2 and P3 of the posterior leaflet 17, whereby the cinching of said segments led to the closure of the gap in coaptation between the anterior leaflet 16 and the posterior leaflet 17 as shown in FIG. 6. In FIG. 7b the mitral valve closes properly.

Figure 8:
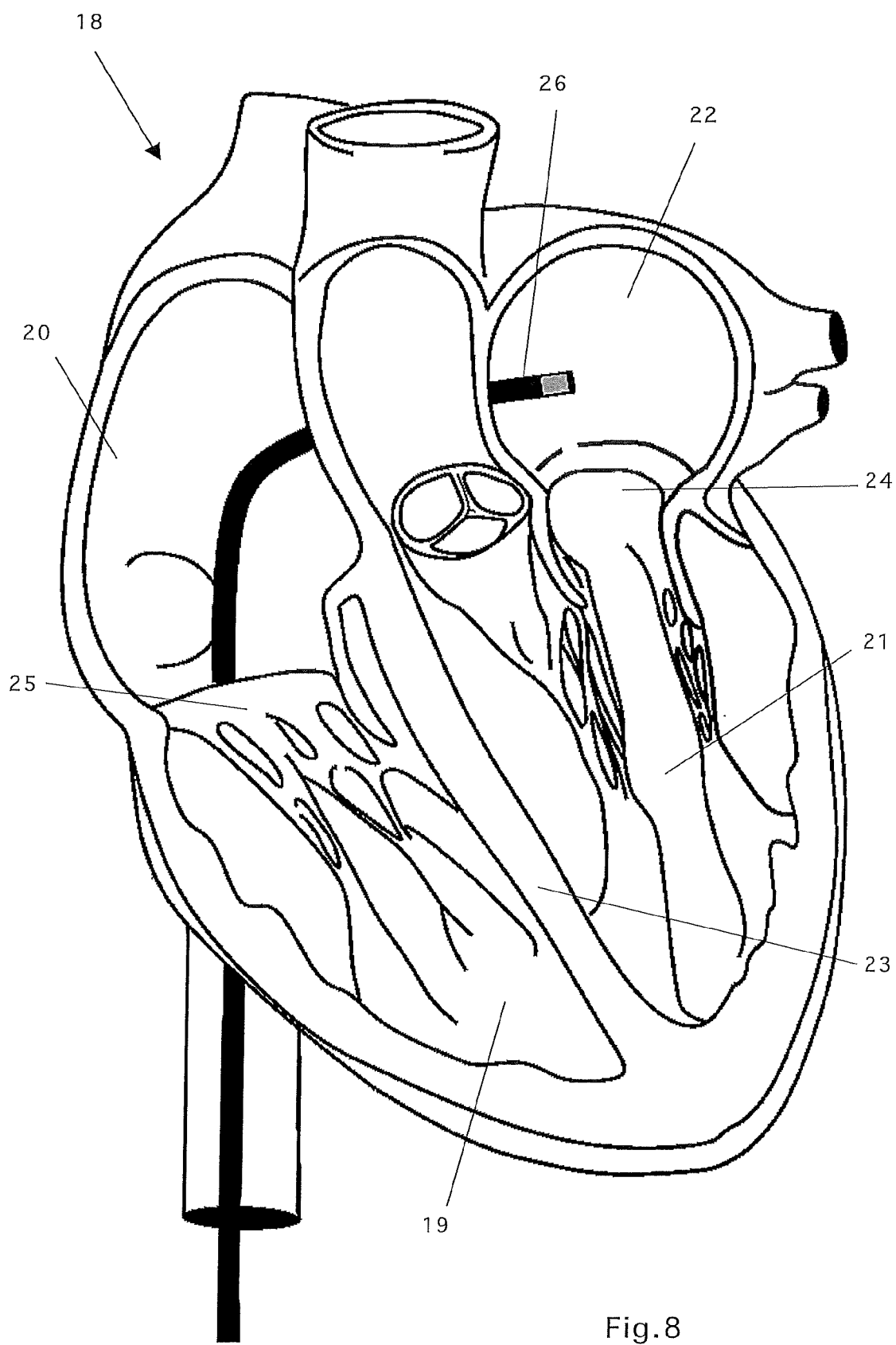
FIG. 8, FIG. 9 and FIG. 10 show the individual stages of implanting the device according to the invention.

FIG. 8 shows a cross sectional illustration of a human heart 18 comprising the right ventricle 19, the right atrium 20, the left ventricle 21 and the left atrium 22. The septum 23 divides the heart 18 in a right and a left section. The mitral valve 24 allows the blood to flow from the left atrium 22 into the left ventricle 21. The tricuspid valve 25 is located between the right atrium 20 and the right ventricle 19.

The annuloplasty device of the invention is configured to be deployed to the heart 18 transcatheterally. In particular, the implant may be delivered transseptally to the heart 18 by means of a catheter 26, i.e. through the septum 23 of the heart as shown in FIG. 8. FIG. 8 shows the implantation state in which the catheter 26 has already punctured the septum 23 of the heart 18 and entered the left atrium 22.

Figure 9:
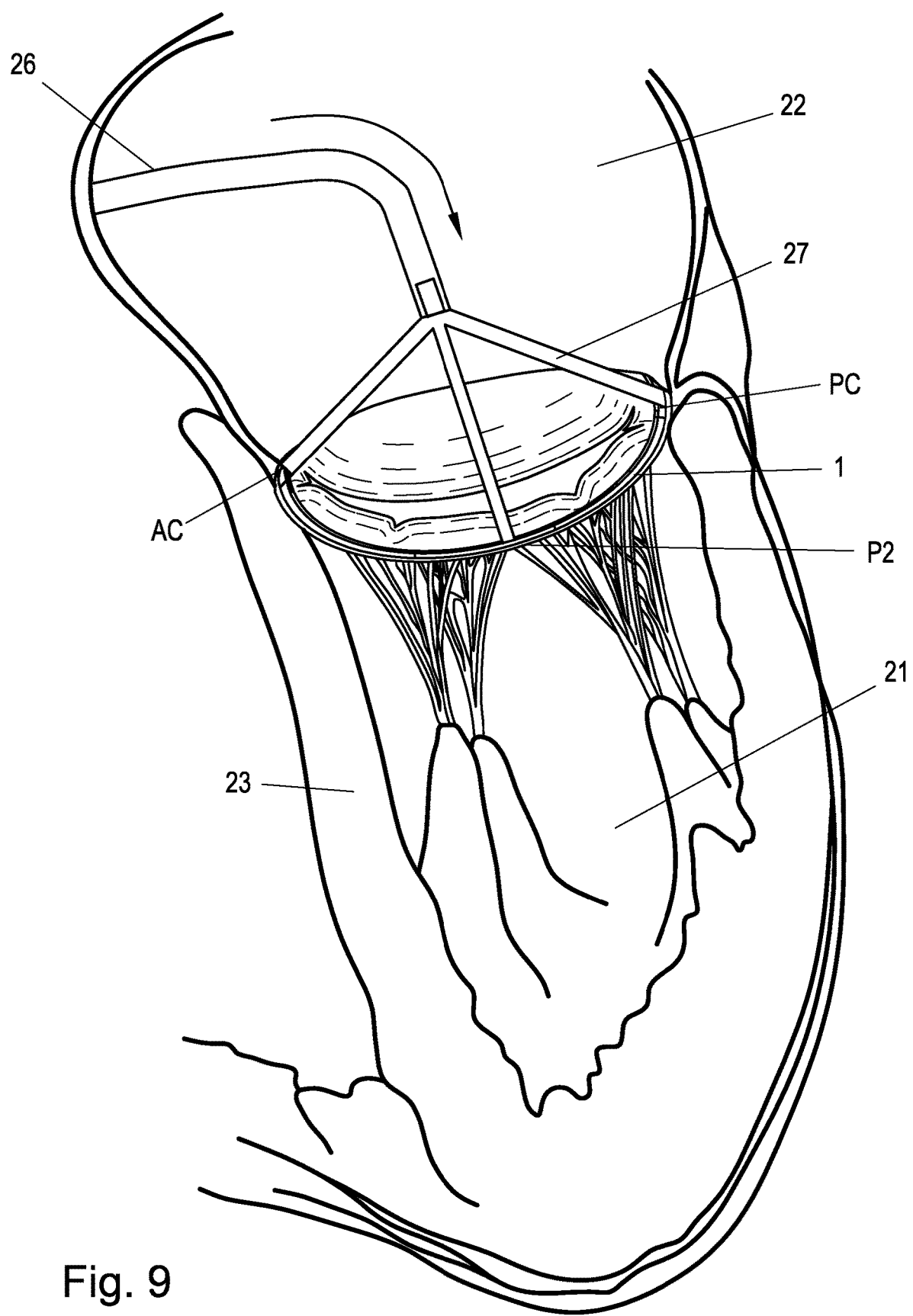

FIG. 9 shows a cross sectional view of the left ventricle 21 and the left atrium 22. Fixing arms 27 were released from the catheter 26 and unfold to fix the center of the annuloplasty device 1 to the P2 region of the posterior leaflet and the ends of the branches of the annuloplasty device 1 to the AC and PC region of the valve, respectively. After the fixing, the annuloplasty device 1 is deployed. FIG. 9 shows the annuloplasty device 1 after having been deployed.

Figure 10:
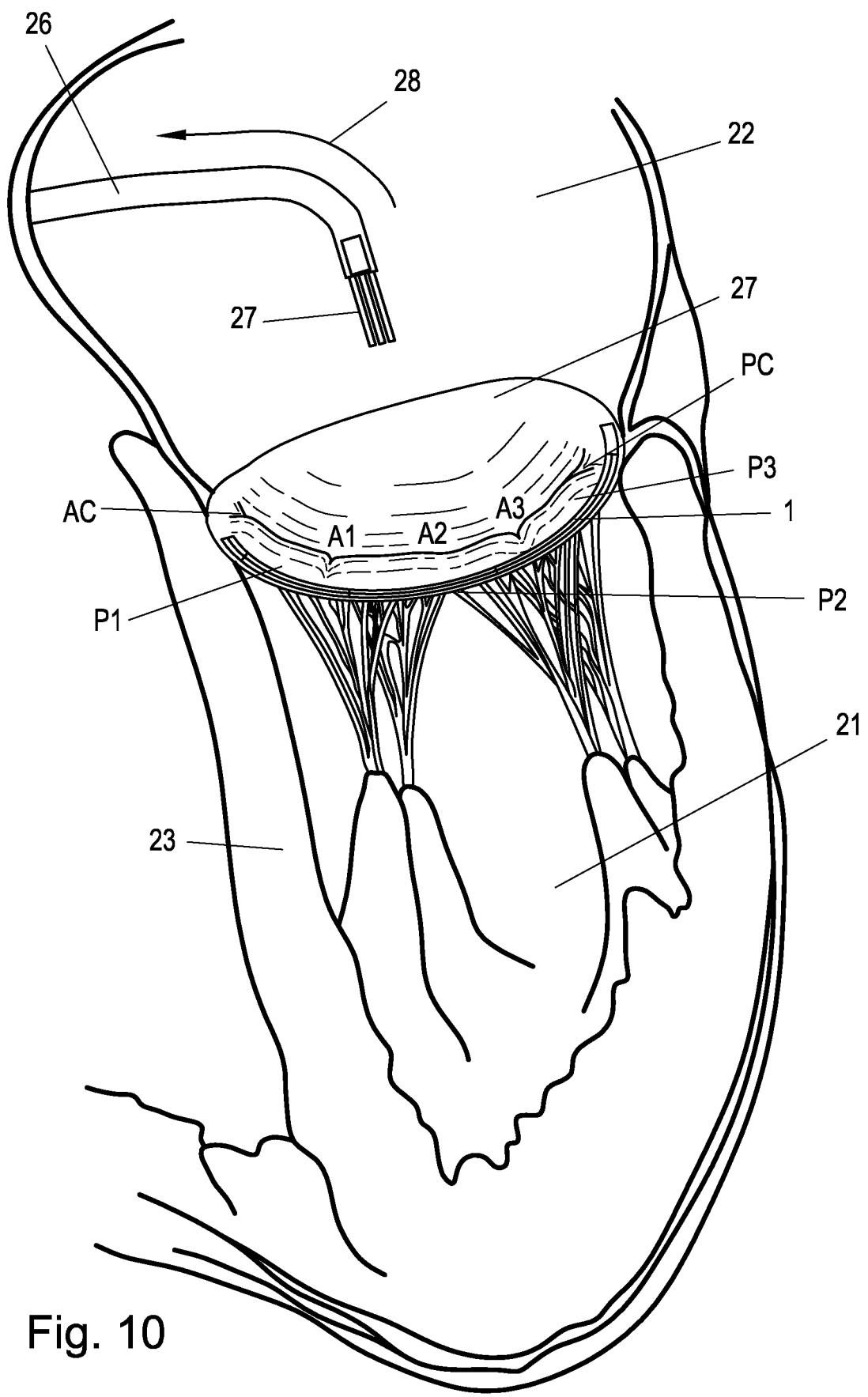

FIG. 10 shows the stage of implantation, in which the annuloplasty device 1 has already been deployed and fixed to the mitral valve and the fixing arms 27 were already detached from the posterior leaflet. The fixing arms 27 are withdrawn from the left atrium 22 with the aid of catheter 26 according to arrow 28. The catheter 27 is also withdrawn from the heart in direction of arrow 28.

The invention claimed is:

1. An annuloplasty device for use on a posterior annulus of a mitral valve, the annuloplasty device being deployable to the mitral valve by a vascular delivery device and positionable along a curvature of the annulus, the annuloplasty device comprising:
   at least a first branch and a second branch, the first branch and the second branch configured to extend along at least a section of the annulus, the first branch and the second branch both having a first end and a second end respectively;
   at least one guiding means for guiding the first and the second branches relative to one another;
   at least one fixing means for fixing the device to the annulus; and
   at least one anchor means arranged on each of the first and second branches;
   wherein the first and the second branches are arranged to be movable relative to one another so that the at least one anchor means engage with the annulus thereby pulling the annulus together when the first and second branches are moved in opposite directions.

2. The annuloplasty device according to claim 1, wherein:
   the first and the second branches are movably guided in the guiding means;
   the device further comprises a first pulling means arranged on the first end of the first branch and a second pulling means arranged on the first end of the second branch; and
   the first ends of the two branches are arranged opposite to one another, and the relative movement of the branches is achieved by pulling the pulling means in opposite directions.

3. The annuloplasty device according to claim 1, further comprising a gear for driving the first and second branches to move relative to each other.

4. The annuloplasty device according to claim 1, wherein:
   a second and a third fixing means are provided;
   the center of the device carries the first fixing means;
   the first end of the first branch carries the second fixing means;
   the first end of the second branch carries the third fixing means; and
   the first ends of the two branches are arranged opposite to one another.

5. The annuloplasty device according to claim 1, wherein the fixing means are formed by at least one of clamps, pliers, needles, hooks, and pins.

6. The annuloplasty device according to claim 1, wherein the at least one first and second branches are half-ring shaped.

7. The annuloplasty device according to claim 1, wherein the anchor means comprise at least one of needles, hooks, clips, staples, and rivets.

8. The annuloplasty device according to claim 1, wherein the at least one anchor means of the first branch is oriented in an opposite direction to the at least one anchor means of the second branch.

9. The annuloplasty device according to claim 1, wherein a plurality of anchor means are arranged on each of the first and the second branches.

10. The annuloplasty device according to claim 1, wherein the anchor means are deployable from a first position, in which the anchor means are retracted for being arranged within a delivery device, into a second position, in which the anchor means are deployed.

11. The annuloplasty device according to claim 9, wherein:
   the device further comprises covering means fixed to one of the first or second branches;
   the covering means enclose the anchor means, when being in the first, retracted position; and
   the anchor means are deployed when the first branch, which carries the covering means, is moved in opposite direction of the second branch, thereby releasing the anchor means.

12. A delivery device with the annuloplasty device according to claim 1 for delivering and deploying the annuloplasty device to the annulus of the mitral valve, comprising:
   at least one flexible tube, in which the annuloplasty device is housed prior to being delivered;
   a guiding wire for guiding the flexible tube to the annulus; and
   retracting means for retracting the flexible tube relative to the at least first and second branches of the annuloplasty device so as to successively release the at least first and second branches from the flexible tube.

* * * * *